（12）United States Patent
Govari et al.

(10) Patent No.: US 10,695,085 B2
(45) Date of Patent: Jun. 30, 2020

(54) TURBINE-DRIVEN ROTARY SINUPLASTY CUTTER

(71) Applicant: Biosense Webster (Israel) Ltd., Yokneam (IL)

(72) Inventors: Assaf Govari, Haifa (IL); Yehuda Algawi, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 417 days.

(21) Appl. No.: 15/234,319

(22) Filed: Aug. 11, 2016

(65) Prior Publication Data

US 2018/0042640 A1    Feb. 15, 2018

(51) Int. Cl.

| | | |
|---|---|---|
| *A61B 17/3207* | (2006.01) | |
| *A61B 17/24* | (2006.01) | |
| *A61B 17/32* | (2006.01) | |
| *F01D 1/06* | (2006.01) | |
| *F01D 15/06* | (2006.01) | |
| *F01D 25/24* | (2006.01) | |
| *A61B 17/00* | (2006.01) | |

(52) U.S. Cl.
CPC ...... *A61B 17/320758* (2013.01); *A61B 17/24* (2013.01); *A61B 17/32002* (2013.01); *F01D 1/06* (2013.01); *F01D 15/06* (2013.01); *F01D 25/24* (2013.01); *A61B 2017/00544* (2013.01); *A61B 2017/00553* (2013.01); *F05D 2220/30* (2013.01); *F05D 2240/12* (2013.01)

(58) Field of Classification Search
CPC ...... A61B 17/320758; A61B 17/32002; A61B 17/24; A61B 2017/00544; A61B 2017/00553; F01D 15/06; F01D 1/06; F01D 25/24; F05D 2220/30; F05D 2240/12
See application file for complete search history.

(56) References Cited

U.S. PATENT DOCUMENTS

| | | | | |
|---|---|---|---|---|
| 4,589,412 A | * | 5/1986 | Kensey | ............... A61B 17/22 604/22 |
| 4,631,052 A | * | 12/1986 | Kensey | .......... A61B 17/320758 604/22 |
| 4,790,813 A | * | 12/1988 | Kensey | ............ A61B 17/22031 604/22 |
| 5,074,750 A | | 12/1991 | Kakimoto | |
| 5,562,446 A | * | 10/1996 | Matsui | ............... A61B 17/1628 433/132 |
| 5,803,733 A | | 9/1998 | Trott et al. | |
| 5,984,654 A | | 11/1999 | Mendoza et al. | |

(Continued)

OTHER PUBLICATIONS

European Search Report for application No. EP17185741 dated Jan. 2, 2018, pp. 7.

*Primary Examiner* — Phong Son H Dang
(74) *Attorney, Agent, or Firm* — Todd J. Burns

(57) ABSTRACT

A surgical apparatus includes a rotatable shaft and a turbine assembly. The rotatable shaft includes a cutter located thereon. The cutter is configured to cut an object when the shaft is rotating about a rotational axis. The turbine assembly includes a turbine and a turbine housing. The turbine housing is configured to receive a fluid that enters the housing parallel to the rotational axis, and to steer the fluid to impinge on the turbine in a direction that is not parallel to the rotational axis. The turbine is configured to rotate the shaft so as to cut the object by the cutter.

7 Claims, 2 Drawing Sheets

(56) References Cited

U.S. PATENT DOCUMENTS

| | | | |
|---|---|---|---|
| 7,811,056 B2 * | 10/2010 | Flock | A61C 1/05 |
| | | | 415/202 |
| 8,562,343 B2 | 10/2013 | Magneson et al. | |
| 8,721,333 B2 | 5/2014 | Takashi et al. | |
| 2001/0005788 A1 * | 6/2001 | McGuckin, Jr. | A61B 17/22 |
| | | | 606/167 |
| 2007/0087307 A1 * | 4/2007 | Flock | A61C 1/05 |
| | | | 433/132 |
| 2009/0234378 A1 * | 9/2009 | Escudero | A61B 17/320758 |
| | | | 606/180 |
| 2010/0121141 A1 * | 5/2010 | Rontal | A61B 1/0051 |
| | | | 600/106 |
| 2013/0266430 A1 | 10/2013 | Hasegawa | |
| 2013/0267891 A1 * | 10/2013 | Malhi | A61M 25/0082 |
| | | | 604/30 |
| 2014/0249448 A1 * | 9/2014 | Furlong | A61B 10/04 |
| | | | 600/563 |
| 2015/0018622 A1 | 1/2015 | Tesar et al. | |
| 2015/0018710 A1 | 1/2015 | Furlong et al. | |
| 2017/0319188 A1 * | 11/2017 | Furlong | A61B 10/0275 |

* cited by examiner

TURBINE-DRIVEN ROTARY SINUPLASTY CUTTER

FIELD OF THE INVENTION

The present invention relates generally to minimally-invasive surgery, and specifically to driving a rotary cutter.

BACKGROUND OF THE INVENTION

Turbine-driven rotary cutters and drillers are used in a variety of medical applications.

For example, U.S. Patent Application Publication 2013/0266430, whose disclosure is incorporated herein by reference, describes an air turbine handpiece having: a head portion with built-in free turbine blade, a neck portion installed consecutively with the head portion and grasped by an operator, a grip portion installed consecutively with the neck portion, an air supply duct for driving the turbine blade, and an exhaust duct for exhausting the air. The exhaust duct is provided with a reflux duct, open at one end to the exhaust duct, and open at the other end to the turbine room as the exhaust exit, a value in which an aperture at the reflux exit of the reflux duct is divided by an aperture in the air supply port of the air supply duct, becomes one or less, and the reflux exit of the reflux duct is opened to the turbine room near the air supply port between the air supply port and the exhaust exit.

U.S. Pat. No. 8,562,343, whose disclosure is incorporated herein by reference, describes a dental handpiece that uses a single airflow input to drive both a rotor and provide a hydrostatic bearing. The fluid flow in the form of compressed air is applied first to the hydrostatic bearings and then subsequently to the turbine blades of the rotor without the use of any moving mechanical parts by the design of the air passageway being more direct for the hydrostatic bearing. This passageway is the form of a manifold insert which may be mounted within the handpiece. The handpiece includes a pair of frusto-conical cages separated by a C-shaped spacer which enables precise fabrication. The frusto-conical ends of the rotor and the mating frusto-conical inner surfaces of the cages are provided with a diamond like carbon coating.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention that is described herein provides a surgical apparatus including a rotatable shaft and a turbine assembly. The rotatable shaft includes a cutter located thereon. The cutter is configured to cut an object when the shaft is rotating about a rotational axis. The turbine assembly includes a turbine and a turbine housing. The turbine housing is configured to receive a fluid that enters the housing parallel to the rotational axis, and to steer the fluid to impinge on the turbine in a direction that is not parallel to the rotational axis. The turbine is configured to rotate the shaft so as to cut the object by the cutter.

In some embodiments, the turbine housing includes one or more fluid channels configured to receive the fluid in a first direction, which is parallel to the rotational axis, and to steer the received fluid to a second direction, different from the first direction, so that the fluid impinges on the turbine from the second direction. In other embodiments, the second direction is orthogonal to the first direction. In yet other embodiments, the fluid channels are adjacent to one another so as to form a contiguous jet of the steered fluid.

In an embodiment, the fluid includes compressed air. In another embodiment, the surgical apparatus further includes one or more fluid outlet tubes, which are configured to evacuate the impinged fluid out of the turbine housing. In yet another embodiment, the fluid outlet tubes are configured to evacuate the impinged fluid parallel to the rotational axis. In some embodiments, the surgical apparatus further includes an exhaust pipe, which is coupled to the cutter and is coaxially disposed in the turbine housing. The exhaust pipe is configured to draw the object away from the surgical apparatus.

There is additionally provided, in accordance with an embodiment of the present invention, a method including, in a surgical apparatus, which includes a turbine assembly including a turbine and a turbine housing, and a rotatable shaft that is coupled to the turbine assembly and includes a cutter, receiving a fluid that enters the turbine housing parallel to a rotational axis of the turbine. The fluid is steered to impinge on the turbine in a direction that is not parallel to the rotational axis. A rotatable shaft is rotated using the turbine, so as to cut an object by the cutter.

The present disclosure will be more fully understood from the following detailed description of the embodiments thereof, taken together with the drawings, in which:

DETAILED DESCRIPTION OF EMBODIMENTS

Overview

Embodiments of the present invention that are described hereinbelow provide improved techniques for driving a rotary cutter attached to a rotatable shaft in a catheter. These techniques can be used, for example, in a sinuplasty procedure, in which the cutter rotates relative to an opening in the insertion tube of the catheter. In some embodiments, the cutter is disposed on the shaft, and therefore, when rotating the shaft during the medical procedure, the cutter also rotates and cuts an object (e.g., a nasal polyp) to be removed.

The catheter further comprises a turbine assembly that rotates the shaft. The turbine assembly comprises a turbine having multiple blades, and a turbine housing. In the disclosed configurations, compressed air enters the turbine housing in a direction that is parallel to the rotational axis of the shaft. The turbine housing steers the compressed air, e.g., to a direction that is orthogonal to the rotational axis, so as to impinge on the turbine blades.

In an embodiment, the turbine housing comprises one or more fluid channels for steering the compressed air that enters the turbine assembly. Each fluid channel comprises one or more inlet nozzles and one or more outlet nozzles. The compressed air enters the inlet nozzle at a direction parallel to the rotational axis of the turbine. The inlet nozzle is shaped so as to steer the air to impinge on the turbine at a direction not parallel (e.g., orthogonal) to the rotational axis. After the air has hit the turbine blades, the outlet nozzles are configured to evacuate the air, through outlet tubes, away from the turbine housing. The blades are configured to rotate the turbine about the rotational axis, together with the shaft and the cutter so as to cut the polyp.

The surgical catheter further comprises an exhaust pipe, which is configured to draw the removed polyp to a drain located at a distal end of the catheter. In an embodiment, the exhaust pipe may be disposed along the rotational axis of the turbine. In this embodiment the fluid channel configuration is typically designed so that the removed polyp will not interfere with the compressed air flowing into the turbine assembly.

The disclosed configurations may be disposable or reusable, and are configured to reduce the overall size and cost of the turbine by receiving the air in parallel to the rotational axis and by reducing the size and cost of the parts. Furthermore, the turbine design and assembly improves the profile of the impinged air on the blades (e.g., symmetrically) so as to increase the overall rotational speed of the shaft.

System Description

Figure 1:
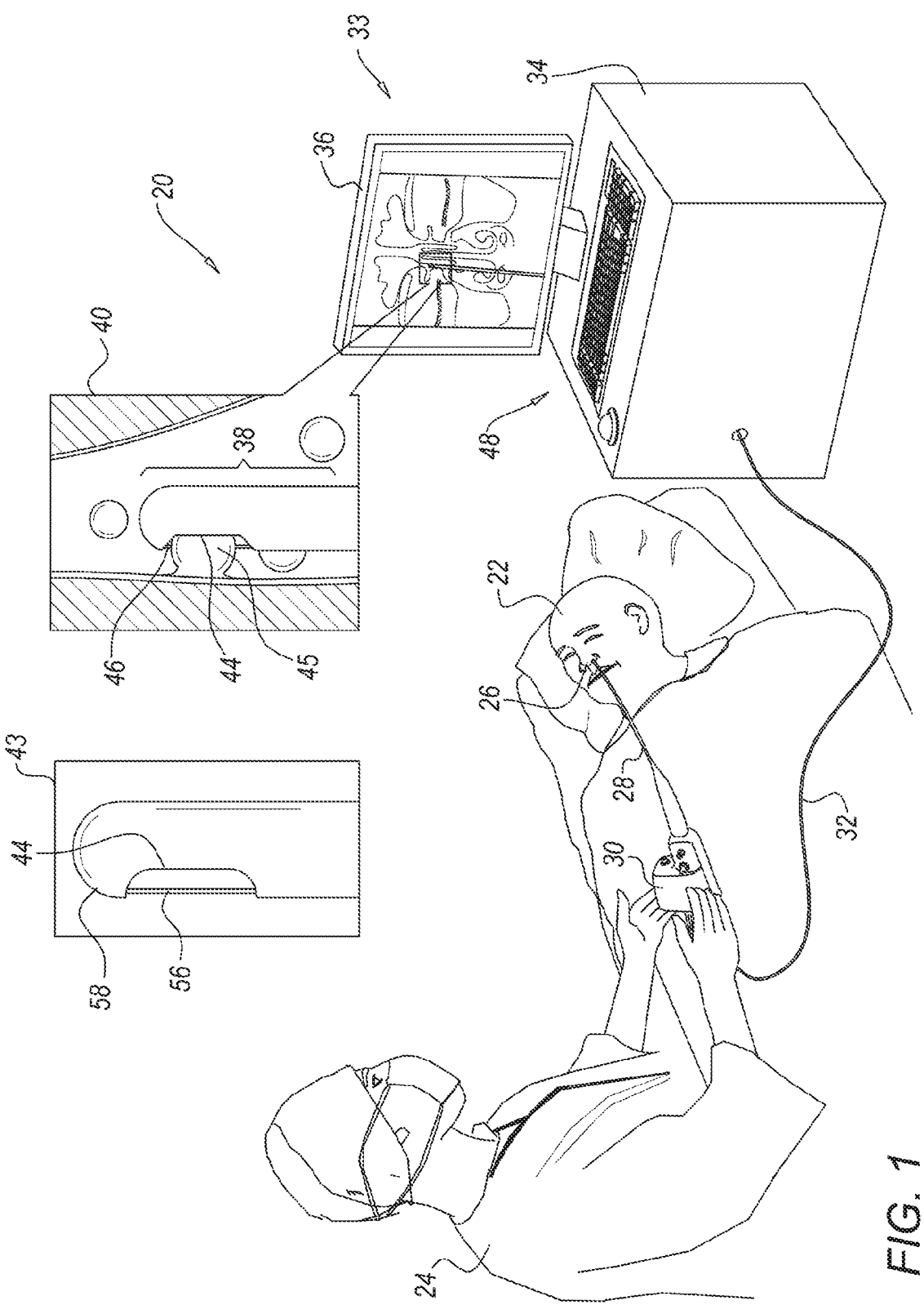
FIG. 1 is a schematic, pictorial illustration of a surgical system, in accordance with an embodiment of the present invention.

FIG. 1 is a schematic pictorial illustration of a sinuplasty procedure using a surgical system 20, in accordance with an embodiment of the present invention. System 20 comprises a surgical catheter 28, which a physician 24 inserts into a nose 26 of a patient 22 so as to remove a foreign object or a tumor, such as a nasal polyp 45 (shown in an inset 40). Catheter 28 comprises a proximal end 30, configured to control a distal end 38 of the catheter.

System 20 further comprises a console 33, which comprises a processor 34, typically a general-purpose computer, with suitable front end and interface circuits for receiving signals from catheter 28, via a cable 32, and for controlling other components of system 20 described herein. Console 33 further comprises input devices 48 and a display 36, which is configured to display the data (e.g., images) received from processor 34 or inputs inserted by a user (e.g., physician 24).

Referring to insets 40 and 43, distal end 38 typically comprises a rigid hollow insertion tube 58 for insertion into the nose of patient 22. Tube 58 is coaxially disposed around a rotatable shaft 56 (shown in inset 43 and FIG. 4). In some embodiments, shaft 56 may be driven using a turbine (shown in FIGS. 3 and 4 and described in detail below) that can rotate clockwise and/or counterclockwise depending on the structure of the turbine and/or the turbine housing.

In some embodiments, tube 58 has an opening 44. Shaft 56 comprises a sinuplasty cutter 46 that is aligned with opening 44 in the insertion tube. Cutter 46 rotates with the shaft and is configured to cut objects such as polyp 45.

Referring to inset 40, during the sinuplasty procedure, physician 24 navigates catheter 28 so that opening 44 is facing polyp 45. In an embodiment, cutter 46 does not block opening 46 so that polyp 45 may be inserted through opening 44 into tube 58. In other embodiments, physician 24 may confirm the position of opening 46 with respect to polyp 45 using mapping techniques such as depicted in U.S. patent application Ser. No. 14/942,455, to Govari et al., filed Nov. 16, 2015, which is incorporated herein by reference.

Once polyp 45 passes through opening 44, physician 24 may use console 33 or proximal end 30 to rotate shaft 56 including cutter 46 so as to remove at least part of polyp 45. In some embodiments, after removing the polyp, physician 24 may rotate shaft 56 to any desired angular position relative to opening 44. For example, as shown in inset 43, physician 24 may rotate shaft 56 so that cutter 46 is facing the right side of tube 58 and the body of shaft 56 blocks opening 44. Catheter 28 draws the removed polyp into a drain (not shown) through an exhaust pipe (shown in FIGS. 2, 3 and 4). The drain may be located, for example, in proximal end 30.

FIG. 1 shows only elements related to the disclosed techniques, for the sake of simplicity and clarity. System 20 typically comprises additional modules and elements that are not directly related to the disclosed techniques, and were thus intentionally omitted from FIG. 1 and from the corresponding description.

Figure 2:
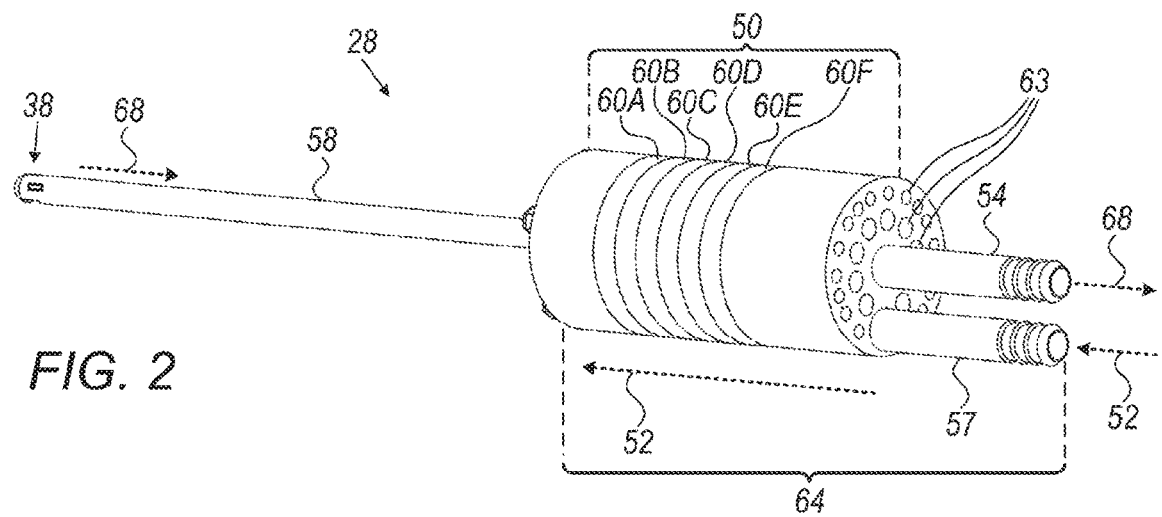
FIG. 2 is a schematic, pictorial illustration of a surgical catheter, in accordance with an embodiment of the present invention.

FIG. 2 is a schematic, pictorial illustration of surgical catheter 28, in accordance with an embodiment of the present invention. Catheter 28 comprises a turbine assembly 64, which is configured to rotate shaft 56 (shown in FIG. 4) disposed within insertion tube 58. Assembly 64 comprises a cylindrical turbine housing 50, a fluid inlet pipe 57, an exhaust pipe 54, and a turbine (shown in FIGS. 3 and 4) coaxially disposed in housing 50.

Exhaust pipe 54 is coupled, through the center of housing 50, to insertion tube 58, and configured to draw the removed polyp into the drain at a direction represented by an arrow 68, as described in FIG. 1 above. Arrow 68 also represents a rotational axis of the turbine as will be depicted in FIGS. 3 and 4 below. Fluid inlet pipe 57 is coupled to housing 50 and configured to insert fluid, such as compressed air or any other suitable gas or liquid, into turbine housing 50. The compressed air enters pipe 57 in a direction depicted by an arrow 52, which is parallel to the rotational axis of the turbine.

Turbine housing 50 comprises one or more fluid channels 60. In the example of FIG. 2 housing 50 comprises six channels denoted channels 60A-60F, but any other suitable number of channels may be used. In an embodiment, the incoming compressed air flows through pipe 57 in the direction parallel to the rotational axis as depicted by arrow 52, into housing 50. The compressed air flows to fluid channel 60F, which steers a first portion of the air to impinge on the turbine in a direction that is not parallel to arrow 52.

The portion of the air not steered by channel 60F continues flowing in parallel to the rotational axis toward the other channels (e.g., channels 60E through 60A). Each channel 60 steers a portion of the air flow that may be substantially similar to the first portion so as to form a total of six uniform sub-flows of compressed air that impinge on the turbine. The impinged air causes the turbine to rotate about the rotational axis. After rotating the turbine, the air exits turbine housing 50 through one or more fluid outlet tubes 63 located at the right end of housing 50.

Figure 3:
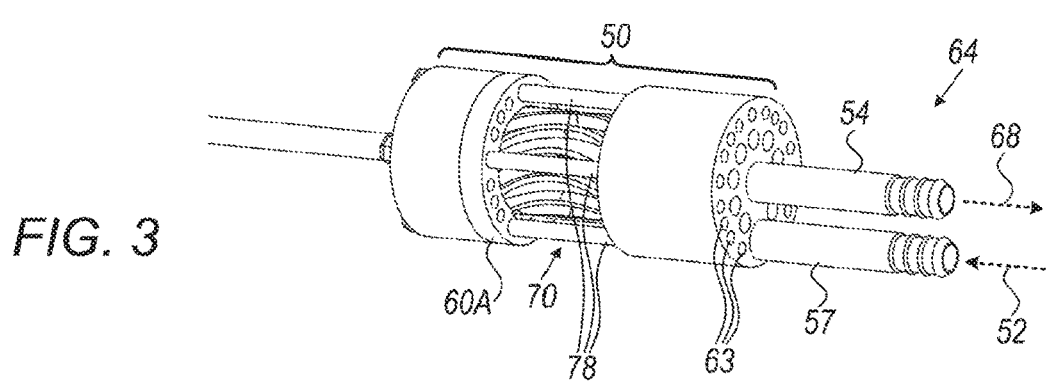
FIG. 3 is a schematic, pictorial illustration of a turbine assembly, in accordance with an embodiment of the present invention.

FIG. 3 is a schematic, pictorial illustration of turbine assembly 64 excluding fluid channels 60B-60F, in accordance with an embodiment of the present invention. Fluid channels 60B-60F are virtually removed for the sake of revealing the internal structure of turbine assembly 64. In some embodiments, assembly 64 comprises multiple (e.g., five) rods 78, on which the fluid channels are threaded. In the example of FIG. 3, three of the rods are threaded through designated holes (shown in FIG. 5) in channel 60A so as to coaxially fit all of the six fluid channels around a turbine 70. As shown in FIG. 2, the six channels are attached to one another so as to form a wide contiguous jet of steered compressed air, but any other suitable arrangement may be applied.

For example, a spacing of a bulk material (not shown) may be disposed between adjacent fluid channels so as to allow the compressed air to flow in parallel to the rotational axis but preventing steering the air toward the turbine at the bulks. In this arrangement, six separate jets of steered air may impinge the turbine blades, rather than a single wide contiguous jet as described with reference to the arrangement shown in FIG. 3. In other embodiments, any number of fluid channels may be used and at least some of the fluid channels may steer different respective portions of air (and/or at different respective directions) so as to form a non-uniform jet of impinged air on the turbine.

Figure 4:
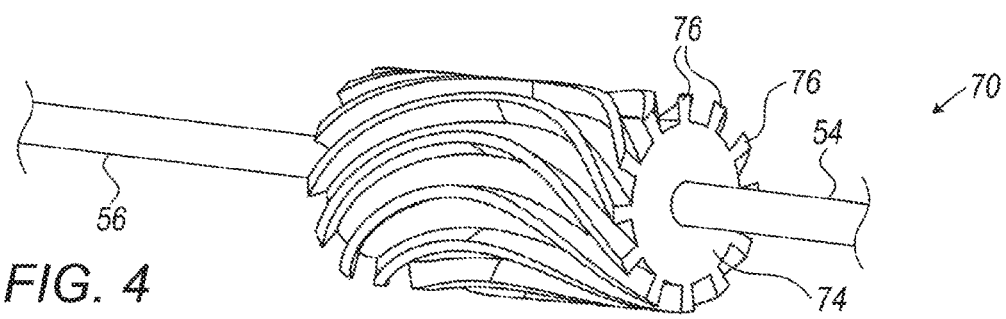
FIG. 4 is a schematic, pictorial illustration of a turbine, in accordance with an embodiment of the present invention.

FIG. 4 is a schematic, pictorial illustration of turbine 70, in accordance with an embodiment of the present invention. Turbine 70 comprises a rotatable drum 74, which is coupled to shaft 56, and configured to rotate the shaft about the rotational axis. Drum 74 has a cylindrical hole through which exhaust pipe 54 draws the removed polyp into the drain (not shown). Turbine 70 further comprises multiple blades 76 on which the steered air impinges, so as to rotate drum 74 and thus shaft 56. After impinging on blades 76 the compressed air exits from housing 50 through outlet tubes 63.

Figure 5:
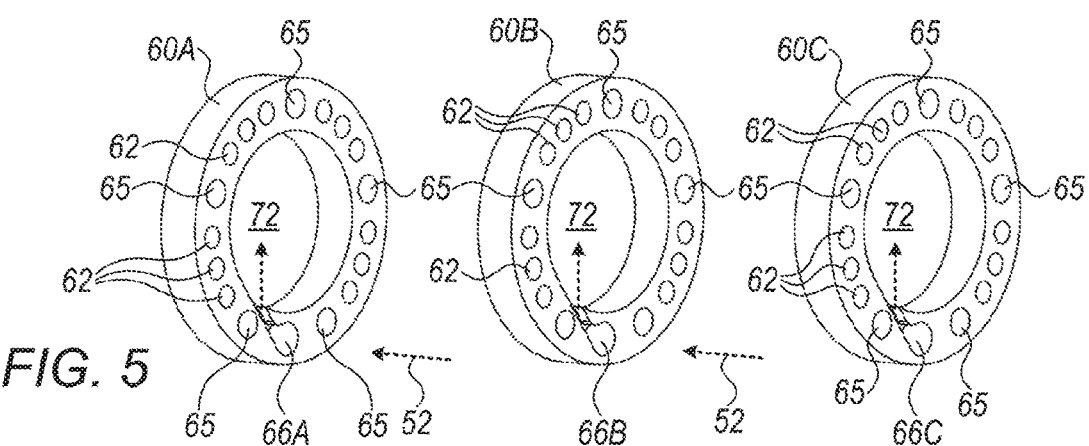
FIG. 5 is a schematic, pictorial illustration of fluid channels in a turbine housing, in accordance with an embodiment of the present invention.

FIG. 5 is a schematic, pictorial illustration of fluid channels 60A, 60B and 60C, in accordance with an embodiment of the present invention. In some embodiments, fluid channels 60A-60F are substantially similar to one another. In an embodiment, fluid channel 60B comprises five holes 65 through which rods 78 are threaded. Channel 60B further comprises a fluid inlet nozzle 66B that receives the air entering pipe 57, through a fluid inlet nozzle 66C, in the direction of arrow 52 (e.g., parallel to the rotational axis). Nozzle 66B is configured to steer a portion of the air to impinge on blades 76 at a direction represented by an arrow 72.

In some embodiments, the steered air may impinge on blades 76 orthogonally to the rotational axis, or at any other suitable direction that is not parallel with the rotational axis. The air pressure as well as the direction of the nozzles (and thus of the impinged air) may be set to determine the desired rotational speed of the shaft. In other embodiments, nozzle 66B is configured to allow the portion of the air not yet steered to continue flowing in parallel to the rotational axis so as to enter channel 60A through a nozzle 66A. In an embodiment, channel 60B comprises one or more (e.g., twelve) fluid outlet nozzles 62 through which the compressed air flows toward outlet tubes 63, after impinging on blades 76.

In alternative embodiments, fluid channels 60 may be formed differently from one another, so as to optimize the rotation force and/or speed applied by the steered air on turbine 70. In an embodiment, turbine 70 is configured to rotate clockwise. In an alternative embodiment, the turbine may be configured to rotate counterclockwise, for example, by flipping the arrangement of nozzles 66 and/or using a different shape of blades 76. In yet alternative embodiments, the compressed air may enter the turbine assembly at any suitable direction that may not be parallel to the rotational axis.

The examples of FIGS. 1-5 refer to a specific configuration of turbine assembly 64, chosen purely for the sake of conceptual clarity. In alternative embodiments, the disclosed techniques can be used, mutatis mutandis, in various other types of surgical catheters. It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

What is claimed is:

1. A surgical apparatus, comprising:
   a rotatable shaft, which comprises
      a cutter located thereon, wherein the cutter is configured to cut an object when the shaft is rotating about a rotational axis; and
   a turbine assembly, which comprises
      a turbine and
      a turbine housing, wherein the turbine housing is configured to receive a fluid that enters the housing parallel to the rotational axis, and to steer the fluid to impinge on the turbine in a direction that is not parallel to the rotational axis, and wherein the turbine is configured to rotate the shaft so as to cut the object by the cutter, and wherein the turbine housing comprises
         a plurality of fluid channels axially arranged and configured to receive the fluid in a first direction, which is parallel to the rotational axis, and to steer the received fluid to a second direction, different from the first direction, so that the fluid impinges on the turbine from the second direction; and
         multiple rods on which the fluid channels are threaded.

2. The apparatus according to claim 1, wherein the second direction is orthogonal to the first direction.

3. The apparatus according to claim 1, wherein the fluid channels are adjacent to one another so as to form a contiguous jet of the steered fluid.

4. The apparatus according to claim 1, wherein the fluid comprises compressed air.

5. The apparatus according to claim 1, and comprising one or more fluid outlet tubes, which are configured to evacuate the impinged fluid out of the turbine housing.

6. The apparatus according to claim 5, wherein the one or more fluid outlet tubes are configured to evacuate the impinged fluid parallel to the rotational axis.

7. The apparatus according to claim 1, and comprising an exhaust pipe, which is coupled to the cutter and is coaxially disposed in the turbine housing, wherein the exhaust pipe is configured to draw the object away from the surgical apparatus.

* * * * *